(12) United States Patent
Cheng et al.

(10) Patent No.: US 8,410,320 B2
(45) Date of Patent: Apr. 2, 2013

(54) METHOD FOR SYNTHESIS OF SECONDARY ALCOHOLS

(75) Inventors: Chien-Hong Cheng, Hsinchu (TW); Jaganathan Karthikeyan, Hsinchu (TW); Pang-Chi Huang, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 224 days.

(21) Appl. No.: 13/045,003

(22) Filed: Mar. 10, 2011

(65) Prior Publication Data

US 2012/0142934 A1    Jun. 7, 2012

(30) Foreign Application Priority Data

Dec. 7, 2010 (TW) .............................. 99142583 A

(51) Int. Cl.
*C07C 29/14* (2006.01)
(52) U.S. Cl. ....................................... 568/881; 568/814
(58) Field of Classification Search .................. 568/881, 568/814
See application file for complete search history.

(56) References Cited

PUBLICATIONS

Yamamoto, Yasunori et al., "Me-Bipam for Enantioselective Ruthenium(II)-Catalyzed Arylation of Aldehydes with Arylboronic Acids", Asymmetric Synthesis, 2009, pp. 4414-4416, vol. 48.
Duan, Hai-Feng et al., "Enantioselective Rhodium-Catalyzed Addition of Arylboronic Acids to Aldehydes Using Chiral Spiro Monophosphite Ligands", Organic Letters, 2006, pp. 1479-1481, vol. 8, No. 7.
Karthikeyan, Jaganathan et al., "Cobalt-Catalyzed Addition Reaction of Organoboronic Acids with Aldehydes: Highly Enantioselective Synthesis of Diarylmethanols", Communication, 2010, pp. 8989-8992, DOI: 10.1002/chem.201001160.

*Primary Examiner* — Elvis O Price
(74) *Attorney, Agent, or Firm* — Muncy, Geissler, Olds & Lowe, PLLC

(57) ABSTRACT

A method for synthesis of secondary alcohols is provided for pharmaceutical secondary alcohol by addition of organoboronic acids with aldehydes in presence of the cobalt ion and bidentate ligands as the catalyst. In addition, an enantioselective synthesis method for secondary alcohols is also herein provided in the present invention. The present invention has advantages in using less expensive cobalt ion and commercially available chiral ligands as the catalyst, wide scope of organoboronic acids and aldehydes compatible with this catalytic reaction and achieving excellent yields and/or enantiomeric excess.

20 Claims, No Drawings

METHOD FOR SYNTHESIS OF SECONDARY ALCOHOLS

BACKGROUND OF THE INVENTION

1. Field of the Invention

The present invention relates to a method for synthesis of secondary alcohols, particularly to a method for synthesis of secondary alcohols by addition of organoboronic acids with aldehydes in presence of the cobalt ion and bidentate ligands.

2. Description of the Prior Art

Chiral secondary alcohols are key structural units present in various biologically and pharmaceutically active compounds. Transition-metal-catalyzed addition of organometallic reagents with aldehydes is a key method for the synthesis of substituted secondary alcohols. Among them, organoboronic reagents have gained much attention due to the advantages of air and moisture stability, low toxicity, and availability. Among the transition-metal-catalysts, rhodium, palladium, platinum and nickel complexes efficiently catalyzed the addition reaction of organoboronic acids with aldehydes. Recently, copper- and iron-catalyzed addition reactions of organoboronic acid with aldehydes were also reported. However, the scope of aldehydes in these addition reactions is rather limited. Only aromatic aldehydes with an electron-withdrawing substituent worked well. Despite the fact that various metal-catalyzed addition reactions of organoboronic acids with aldehydes are available in the literature, only a few reports on asymmetric reactions were discussed.

Zhou et al. (Org. Lett. 2006, 8, 1479) reported a rhodium-catalyzed enantioselective addition reaction of aromatic boronic acids with aromatic aldehydes. In the reaction, enantiomeric excess (ee) values of 62-87% for chiral biaryl methanols were observed.

Recently, Miyaura et al (Angew. Chem. Int. Ed. 2009, 48, 4414) reported a ruthenium-catalyzed enantioselective addition reaction of aromatic boronic acids with aromatic aldehydes. In the reaction, the expected chiral biaryl methanols were observed in excellent enantiomeric excess. However, in these reactions specially designed chiral ligands and expensive ruthenium or rhodium catalysts were used.

To sum up, the development of new, mild and convenient methods using a low-cost catalyst for the synthesis of chiral secondary alcohols remains highly attractive.

SUMMARY OF THE INVENTION

The present invention is directed to a method for synthesis of secondary alcohols provided for pharmaceutical secondary alcohol by addition of organoboronic acids with aldehydes in presence of the cobalt ion and bidentate ligands as the catalyst.

According to one embodiment, a method for synthesis of secondary alcohols where an organoboronic acid and an aldehyde are reacted in a reaction reagent to obtain a secondary alcohol is disclosed, wherein the reaction reagent comprises a cobalt ion and a bidentate ligand.

The present invention is also directed to an enantioselective method for synthesis of secondary alcohols provided for enantioselective secondary alcohol by addition of organoboronic acids with aldehydes in presence of the cobalt ion and bidentate chiral ligands as the catalyst.

According to another embodiment of the present invention, an enantioselective method for synthesis of secondary alcohols where an organoboronic acid and an aldehyde in an organic reagent are reacted to obtain an enantioselective secondary alcohol, wherein the organic reagent comprises a cobalt ion and a chiral bidentate ligand.

Other advantages of the present invention will become apparent from the following descriptions taken in conjunction with the accompanying drawings wherein certain embodiments of the present invention are set forth by way of illustration and examples.

DESCRIPTION OF THE PREFERRED EMBODIMENT

The present invention is directed to a method for synthesis of secondary alcohols by addition of organoboronic acids with aldehydes in a reaction reagent including cobalt ion and bidentate ligands conjugated thereto as the catalyst.

The organoboronic acids of the present invention may include alkyl and/or aryl boric acid. Preferably, the organoboronic acids are aryl boric acids, particularly phenyl boric acids, which is represented by structural formula (1):

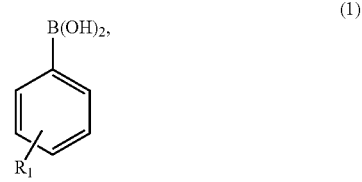

(1)

wherein $R_1$ is a member selected from the group consisting of H, halo, cyano, trifluoromethyl, amino, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl and heteroaryl.

The aldehydes of the present invention are represented by the structural formula (2):

(2)

wherein $R_2$ is a member selected from the group consisting of $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl and heteroaryl.

Alkyl, alkenyl, alkynyl, cycloalkyl, cycloalkenyl, heterocycloalkyl, heterocycloalkenyl, aryl and heteroaryl mentioned herein include both substituted and unsubstituted moieties, unless specified otherwise. Possible substituents on cycloalkyl, cycloalkenyl, heterocycloalkyl, heterocycloalkenyl, aryl, and heteroaryl include, but are not limited to, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, $C_1$-$C_{10}$ alkoxy, aryl, aryloxy, heteroaryl, heteroaryloxy, amino, $C_1$-$C_{10}$ alkylamino, $C_1$-$C_{20}$ dialkylamino, arylamino, diarylamino, $C_1$-$C_{10}$ alkylsulfonamino, arylsulfonamino, $C_1$-$C_{10}$ alkylimino, arylimino, $C_1$-$C_{10}$ alkylsulfonimino, arylsulfonimino, hydroxyl, halo, thio, $C_1$-$C_{10}$ alkylthio, arylthio, $C_1$-$C_{10}$ alkylsulfonyl, arylsulfonyl, acylamino, aminoacyl, aminothioacyl, amido, amidino, guanidine, ureido, thioureido, cyano, nitro, nitroso, azido, acyl, thioacyl, acyloxy, carboxyl, and carboxylic ester. On the other hand, possible substituents on alkyl, alkenyl, or alkynyl include all of the above-recited substituents except $C_1$-$C_{10}$ alkyl. Cycloalkyl, cycloalkenyl, heterocycloalkyl, heterocycloalkenyl, aryl, and heteroaryl can also be fused with each other.

In one embodiment, diaryl methanols may be obtained as product by using reactants arylboronic acid and aryl aldehyde.

The cobalt ion used in the present invention may be $Co^{2+}$ or $Co^{3+}$, preferably $Co^{2+}$, and may be provided by $Co(acac)_2$, $CoI_2$, $CoBr_2$ or $CoCl_2$ The bidentate ligands used in the present invention, for example, include phosphor, nitrogen or oxygen and is used for conjugating with cobalt ion as the catalyst.

For example, bidentate ligands containing phosphor may include DPPE (1,2-bis(diphenylphosphino)ethane), (R)-Prophos ((R)-(+)-1,2-bis(diphenylphosphino)propane), (R)-Tol-BINAP ((R)-(+)-2,2'-Bis(di-p-tolylphosphino)-1,1'-binaphthyl), (S)-BINAP ((S)-(−)-2,2'-Bis(diphenylphosphino)-1,1'-binaphthyl), (S,S)-Chiraphos ((2S,3S)-(−)-bis(diphenylphosphino)butane), (R,R)-BDPP (2R,4R)-(+)-2,4-bis(diphenylphosphino)pentane), (S,S)-BDPP (2S,4S)-(+)-2,4-bis(diphenylphosphino)pentane), (R,R)-Ph-BPE ((−)-1,2-Bis((2R,5R)-2,5-diphenylphospholano)ethane), (R)-Quinap ((R)-(+)-1-(2-diphenylphosphino-1-naphthyl)isoquinoline), (R)-MOP ((R)-(+)-2-(diphenylphosphino)-2'-methoxy-1,1'-binaphthyl), (S,S)-DIPAMP ((S,S)-1,2-Bis[(2-methoxyphenyl)(phenylphosphino)]ethane), (R)-Monophos ((R)-(−)-(3,5-Dioxa-4-phospha-cyclohepta[2,1-a:3,4-a']dinaphthalen-4-yl)dimethylamine) or (S,S)-DIOP ((4S,5S)-(+)-4,5-Bis(diphenylphosphinomethyl)-2,2-dimethyl-1,3-dioxolane).

For example, bidentate ligands containing nitrogen may include 3,5-dimethyl-bispyrazolylmethane, 2,2'-bipyridine or 1,1-bis[4,4-dimethyl-1,3-oxazolin-2-yl]ethane.

For example, bidentate ligands containing oxygen may include (S)-BINOL ((S)-(−)-1,1'-Bi(2-napthol)).

Also in one embodiment, the reaction reagent of the present invention is basic and provided by $K_2CO_3$; however, this is a preferred embodiment and is not thus limited.

Referring to Table 1 and the reaction formula listed below, in one embodiment of the present invention, a secondary alcohol 3 may be obtained from reaction of an arylboronic acid 1 and an aldehyde 2 in presence of the cobalt ion and bidentate ligand as the catalyst.

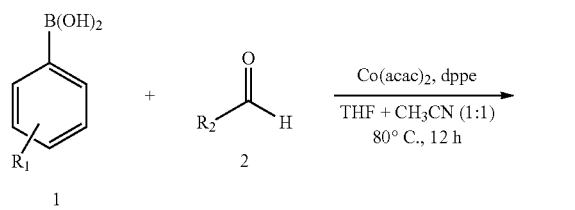

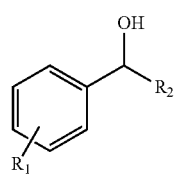

TABLE 1

Results of the addition reaction of arylboronic acid with aldehydes[a]

| Entries | Reactant | Product | Yield[b] [%] |
|---|---|---|---|
| 1 | 1a: $R_1$ = H; 2a: $R_2$ = 4-CN—$C_6H_4$ | 3aa | 96 |
| 2 | 1a: $R_1$ = H; 2b: $R_2$ = 4-$NO_2$—$C_6H_4$ | 3ab | 97 |
| 3 | 1a: $R_1$ = H; 2c: $R_2$ = 4-CHO—$C_6H4$ | 3ac | 93 |
| 4 | 1a: $R_1$ = H; 2d: $R_2$ = 4-$CO_2$Me—$C_6H_4$ | 3ad | 98 |
| 5 | 1a: $R_1$ = H; 2e: $R_2$ = 4-$CF_3$—$C_6H_4$ | 3ae | 89 |
| 6 | 1a: $R_1$ = H; 2f: $R_2$ = 4-F—$C_6H_4$ | 3af | 92 |
| 7 | 1a: $R_1$ = H; 2g: $R_2$ = 3-F—$C_6H_4$ | 3ag | 82 |
| 8 | 1a: $R_1$ = H; 2h: $R_2$ = 2-F—$C_6H_4$ | 3ah | 80 |
| 9 | 1a: $R_1$ = H; 2i: $R_2$ = 4-Cl—$C_6H_4$ | 3ai | 96 |
| 10 | 1a: $R_1$ = H; 2j: $R_2$ = 4-Br—$C_6H_4$ | 3aj | 84 |
| 11 | 1a: $R_1$ = H; 2k: $R_2$ = Ph | 3ak | 73 |
| 12 | 1a: $R_1$ = H; 2l: $R_2$ = 1-napthyl | 3al | 75 |
| 13 | 1a: $R_1$ = H; 2m: $R_2$ = 2-napthyl | 3am | 75 |
| 14 | 1a: $R_1$ = H; 2n: $R_2$ = 4-Me—$C_6H_4$ | 3an | 67 |
| 15 | 1a: $R_1$ = H; 2o: $R_2$ = 4-OMe—$C_6H_4$ | 3ao | 57 |
| 16 | 1a: $R_1$ = H; 2p: $R_2$ = 4-pyridinyl | 3ap | 76 |
| 17 | 1a: $R_1$ = H; 2q: $R_2$ = 2-furyl | 3aq | 69 |
| 18 | 1a: $R_1$ = H; 2r: $R_2$ = 2-thienyl | 3ar | 78 |
| 19 | 1a: $R_1$ = H; 2s: $R_2$ = cyclohexyl | 3as | 79 |
| 20 | 1b: $R_1$ = 4-Br; 2d: $R_2$ = 4-$CO_2$Me—$C_6H_4$ | 3bd | 93 |
| 21 | 1c: $R_1$ = 4-F; 2d: $R_2$ = 4-$CO_2$Me—$C_6H_4$ | 3cd | 93 |
| 22 | 1d: $R_1$ = 4-CHO; 2d: $R_2$ = 4-$CO_2$Me—$C_6H_4$ | 3dd | 84 |
| 23 | 1e: $R_1$ = 4-Me; 2d: $R_2$ = 4-$CO_2$Me—$C_6H_4$ | 3ed | 92 |
| 24 | 1f: $R_1$ = 4-OMe; 2d: $R_2$ = 4-$CO_2$Me—$C_6H_4$ | 3fd | 97 |
| 25 | 1g: $R_1$ = 2-OMe; 2d: $R_2$ = 4-$CO_2$Me—$C_6H_4$ | 3gd | 96 |
| 26 | 1h: $R_1$ = 4-viny; 2d: $R_2$ = 4-$CO_2$Me—$C_6H_4$ | 3hd | 75 |
| 27 | 1i: $R_1$ = (E)-styryl; 2d: $R_2$ = 4-$CO_2$Me—$C_6H_4$ | 3id | 78 |

[a]Unless otherwise mentioned, all of the reactions were carried out by using arylboronic acid 1 (1.20 mmol), aldehydes 2 (1.00 mmol), $Co(acac)_2$ (5 mol %), dppe (5 mol %), and THF/$CH_3CN$ (1:1) at 80° C. for 12 h.
[b]Isolated yields.

EXAMPLES 3aa~3 as

In the above-mentioned reaction condition, various secondary alcohols were obtained from the addition reaction of phenylboronic acid 1a with aromatic aldehydes, heterocyclic aldehydes, and aliphatic aldehydes. Here, benzaldehydes with electron-withdrawing groups, such as 4-$NO_2$ (2b), 4-CHO (2c), 4-$CO_2$Me (2d), and 4-$CF_3$ (2e) provided diarylmethanols 3ab-3ae in excellent yields (89-97%; Table 1, entries 2-5).

Halo-substituted benzaldehyde derivatives are also compatible with the present catalytic reaction. For example, 4-F (2H), 3-F (2g), 2-F (2h), 4-Cl (2i), and 4-Br (2j) also reacted efficiently with 1a to give the corresponding diarylmethanols 3af-3aj in good to excellent yields (Table 1, entries 6-10).

Similarly, benzaldehyde (2k), 1-napthaldehyde (2l) and 2-napthaldehyde (2m) underwent addition reaction with 1a to afford products 3ak-3am in good yields (Table 1, entries 11-13).

Benzaldehydes containing electron-donating groups, such as 4-Me (2n) and 4-OMe (2o) also gave addition products 3an and 3ao albeit in moderate yields (Table 1, entries 14 and 15).

Heterocyclic aldehydes, including 4-formylpyridine (2p), 2-formylfuran (2q), and 2-formylthiophene (2r) also reacted efficiently to give addition products 3ap-3ar in 76, 69, and 78% yields, respectively (Table 1, entries 16-18).

Aliphatic aldehyde, such as cyclohexanecarbaldehyde (2s), also effectively participated in the addition reaction affording product 3 as in 79% yield (Table 1, entry 19).

EXAMPLES 3bd-3id

In addition, various substituted organoboronic acids were reacted with methyl 4-formyl benzoate (2d). Substituents 4-Bromo (1b), 4-fluoro (1c), 4-formyl (1d), 4-methyl (1e), 4-methoxy (1f), 2-methoxy (1g) and 4-vinylphenylboronic (1h) acids all reacted effectively with 2d to furnish substituted diarylmethanols 3bd-3hd in 93, 93, 84, 92, 97, 96, and 75% yield, respectively (Table 1, entries 20-26).

These results clearly indicate that the present addition reaction shows excellent tolerance towards Br, F, CHO, Me, and OMe functional groups.

The catalytic reaction also worked very well with alkenylboronic acid. Thus, (E)-1-styrylboronic acid (1l) reacted with 2d to afford allylic alcohol 3ld in 78% yield (Table 1, entry 27).

Example Results with Different Catalysts Used

Treatment of phenylboronic acid (1a) with 4-cyanobenzaldehyde (2a) in presence of Co(acac)$_2$ (5 mol %), 1,2-bis (diphenylphosphino)ethane (dppe; 5 mol %) in THF/CH$_3$CN (1/1) at 80° C. for 12 h gave addition product 3aa in 96% isolated yield (Table 1, entry 1).

In the present reaction, no extra base was required and only 1.2 mmol of boronic acid was used. The catalytic reaction also worked equally well using CoI$_2$ or CoCl$_2$ (5 mol %), dppe (5 mol %) as the catalyst, and THF as solvent to afford 3aa in 96-97% yield, but base (K$_2$CO$_3$ (1.50 equiv)) was needed to activate the boronic acid.

Enantioselective Secondary Alcohols

Referring to Table 2 and the reaction formula listed below, the present invention is also directed to a secondary alcohol 3 obtained from reaction of an arylboronic acid 1 and an aldehyde 2 in presence of the cobalt ion and bidentate ligand as the catalyst.

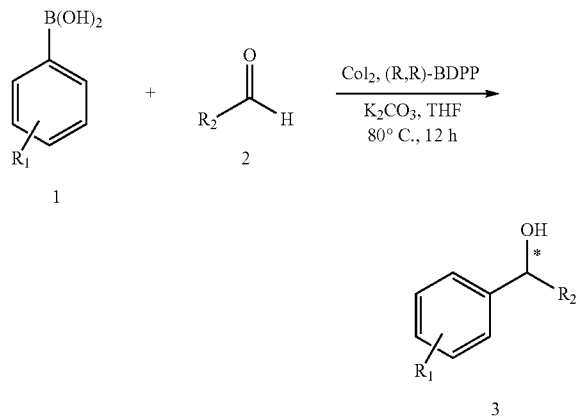

TABLE 2

Results of the enantioselective addition reaction of various phenylboronic acids with substituted aldehydes.[a]

| Entries | Reactant | Product | Yield[b] (ee)[%] |
|---|---|---|---|
| 1 | 1a: R$_1$ = H; 2a: R$_2$ = 4-CN—C$_6$H$_4$ | (S)-3aa | 97 (92) |
| 2 | 1a: R$_1$ = H; 2b: R$_2$ = 4-NO2—C$_6$H$_4$ | (S)-3ab | 95 (93) |
| 3 | 1a: R$_1$ = H; 2d: R$_2$ = 4-CO$_2$Me—C$_6$H$_4$ | (S)-3ad | 98 (94) |
| 4 | 1a: R$_1$ = H; 2d: R$_2$ = 4-CO$_2$Me—C$_6$H$_4$ | (R)-3ad | 95[c] (93) |
| 5 | 1a: R$_1$ = H; 2e: R$_2$ = 4-CF3—C$_6$H$_4$ | (S)-3ae | 97 (92) |
| 6 | 1a: R$_1$ = H; 2f: R$_2$ = 4-F—C$_6$H$_4$ | (S)-3af | 95 (99) |
| 7 | 1a: R$_1$ = H; 2i: R$_2$ = 4-Cl—C$_6$H$_4$ | (S)-3ai | 97 (93) |
| 8 | 1a: R$_1$ = H; 2j: R$_2$ = 4-Br—C$_6$H$_4$ | (S)-3aj | 97 (96) |
| 9 | 1a: R$_1$ = H; 2l: R$_2$ = 1-naphtyl | (S)-3al | 77 (89) |
| 10 | 1a: R$_1$ = H; 2m: R$_2$ = 2-napthyl | (S)-3am | 89 (92) |
| 11 | 1a: R$_1$ = H; 2n: R$_2$ = 4-Me—C$_6$H$_4$ | (S)-3an | 90 (93) |
| 12 | 1a: R$_1$ = H; 2o: R$_2$ = 4-OMe—C$_6$H$_4$ | (S)-3ao | 85 (92) |
| 13 | 1a: R$_1$ = H; 2r: R$_2$ = 2-thienyl | (S)-3ar | 82 (86) |
| 14 | 1a: R$_1$ = H; 2s: R$_2$ = cyclohexyl | (R)-3as | 84 (97) |
| 15 | 1b: R$_1$ = 4-Br; 2d: R$_2$ = 4-CO$_2$Me—C$_6$H$_4$ | (+)-3bd | 99 (90) |
| 16 | 1b: R$_1$ = 4-Br; 2k: R$_2$ = Ph | (R)-3bk (R)-3aj | 84 (94) |
| 17 | 1e: R$_1$ = 4-Me; 2k: R$_2$ = Ph | (R)-3ek (R)-3an | 91 (95) |
| 18 | 1f: R$_1$ = 4-OMe; 2k: R = Ph | (R)-3fk (R)-3ao | 93 (94) |
| 19 | 1e: R$_1$ = 4-Me; 2d: R = 4-CO$_2$Me—C$_6$H$_4$ | (+)-3ed | 95 (91) |
| 20 | 1f: R$_1$ = 4-OMe; 2d: R = 4-CO$_2$Me—C$_6$H$_4$ | (+)-3fd | 97 (94) |
| 21 | 1g: R$_1$ = 2-OMe; 2d: R = 4-CO$_2$Me—C$_6$H$_4$ | (+)-3gd | 92 (90) |

[a]Unless otherwise mentioned, all of the reactions were carried out by using arylboronic acid 1 (1.50 mmol), aldehydes 2 (1.00 mmol), CoI$_2$ (5 mol %), (R,R)-BDPP (5 mol %), K$_2$CO$_3$ (1.5 equiv) and THF (2.0 ml) at 80° C. for 12 h.
[b]Isolated yields.
[c](S,S)-BDPP was used.

Examples for Selecting Ligands and Cobalt Ions

Various bidentate chiral ligands, including (R)-Prophos, (R)-Tol-BINAP, (S)-BINAP, (S,S)-Chiraphos, (S)-BINOL, (R,R)-Ph-BPE, (R)-Quinap, (R)-MOP, (S,S)-DIPAMP, (R)-Monophos, (R,R)-BDPP, (S,S)-BDPP and (S,S)-DIOP, were adopted and examined in the present invention.

Phenylboronic acid (1a) and 2d were used as the model substrates in this study, where cobalt catalyst CoI$_2$ (5 mol %), a bidentate chiral ligand (5 mol %), and K$_2$CO$_3$ (1.5 equiv) in THF were used. Among the tested ligands, (R,R)-BDPP is most effective, affording (S)-diarylmethanol 3ad in 98% yield with an ee value of 94% (Table 2, entry 3). Other ligands provided 3ad in 44-86% yields with an ee value of 10-67%.

Under the reaction conditions, (S,S)-BDPP provided the other enantiomer (R)-diarylmethanol 3ad in 95% yield with an ee of 93% (Table 2, entry 4).

Another cobalt catalyst, C (acac)$_2$/(R,R)-BDPP, in THF without base is also effective, giving chiral (S)-3ad in 95% yield and 93% ee.

EXAMPLES 3aa-3 as

Referring to Table 2 and the reaction formula, in presence of CoI$_2$ (5 mol %)/(R,R)-BDPP (5 mol %) and K$_2$CO$_3$ (1.5 equiv) in THF, the reaction of various substituted aldehydes with phenylboronic acid (1a) were then examined.

Electron-withdrawing groups, 4-CN (2a), 4-NO$_2$ (2b), 4-CO$_2$Me (2d), and 4-CF$_3$ (2e) substituted benzaldehydes afforded chiral (S)-diarylmethanols 3aa, 3ab, 3ad, and 3ae in excellent 97, 95, 98, and 97% yield with 92, 93, 94 and 92% ee, respectively (Table 2, entries 1-3, 5).

Also, if CoI$_2$/(S,S)-BDPP was employed as the catalyst, the reaction of 1a with 2d afforded the corresponding (R)-3ad in 93% ee (Table 2, entry 4).

Similarly, by using CoI$_2$/(R,R)-BDPP as the catalyst, 4-F (2f), 4-Cl (2i) and 4-Br (2j) substituted benzaldehydes may effectively react with phenylboronic acid 1a providing (S)-diarylmethanols 3af, 3ai and 3aj in excellent 95-97% yield with 99, 93, and 96% ee, respectively (Table 2, entries 6-8).

Likewise, 1-naphth (2l) and 2-naphthaldehyde (2m), 4-methyl (2n), 4-methoxybenzaldehyde (2o), and 2-formylthiophene (2r) gave (S)-diarylmethanols 3al, 3am, 3an, 3ao, and 3ar, respectively, in 77-90% yield with 86-93% ee (Table 2, entries 9-13).

In a similar manner, cyclohexanecarbaldehyde (2s) yielded (R)-3 as in 84% yield with 97% ee (Table 2, entry 14).

EXAMPLES 3bd, 3ed, 3fd and 3gd

In addition, other substituted phenylboronic acids, including 4-bromo (1b), 4-methyl (1e), 4-methoxy (1f), and 2-methoxy (1g) phenylboronic acids, also reacted smoothly with 4-CO$_2$Me substituted benzaldehyde 2d to give diarylmethanols 3bd, 3ed, 3fd, and 3gd in excellent yields (92-99%) and ee values (90-94%), respectively (Table 2, entries 15, 19-21).

It is noteworthy that (R)-3bk is the enantiomer of (S)-3aj (Table 2, entry 8) prepared from phenylboronic acid (1a) and 4-bromobenzaldehyde (2j) using the same chiral CoI$_2$/(R,R)-BDPP catalyst.

In a similar manner, product (R)-3ek (Table 2, entry 17) is enantiomer of (S)-3an (Table 2, entry 11) and (R)-3fk (Table 2, entry 18) is the enantiomer of (S)-3ao (Table 2, entry 12).

Thus, the present catalytic asymmetric addition reaction provides a versatile method to prepare the two enantiomers by using the same chiral catalyst. Moreover, in the present asymmetric reaction, products (S)-3ai and (R)-3ek are known to be the key intermediates for biologically active compounds (S)-cetirizine and (R)-neobenodine, respectively.

To sum up, the method for synthesis of secondary alcohols of the present invention may obtain pharmaceutical secondary alcohol with excellent yields and/or enantiomeric excess by addition of organoboronic acids with aldehydes in presence of the cobalt ion and bidentate ligands as the catalyst. The present invention may also have advantages in using less expensive cobalt ion and commercially available chiral ligands (such as (R,R)-BDPP) as the catalyst and wide scope of organoboronic acids and aldehydes compatible with this catalytic reaction.

While the invention can be subject to various modifications and alternative forms, a specific example thereof has been shown in the drawings and is herein described in detail. It should be understood, however, that the invention is not to be limited to the particular form disclosed, but on the contrary, the invention is to cover all modifications, equivalents, and alternatives falling within the spirit and scope of the appended claims.

What is claimed is:

1. A method for synthesis of secondary alcohols, comprising:
    reacting an organoboronic acid and an aldehyde in a reaction reagent to obtain a secondary alcohol, wherein the reaction reagent comprises a cobalt ion and a bidentate ligand.

2. The method as claimed in claim 1, wherein the organoboronic acid is an arylboronic acid.

3. The method as claimed in claim 1, wherein the organoboronic acid is a phenylboronic acid represented by a structure formula (1):

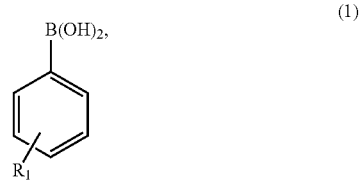

wherein R$_1$ is a member selected from the group consisting of H, halo, cyano, trifluoromethyl, amino, C$_1$-C$_{10}$ alkyl, C$_2$-C$_{10}$ alkenyl, C$_2$-C$_{10}$ alkynyl, C$_3$-C$_{20}$ cycloalkyl, C$_3$-C$_{20}$ cycloalkenyl, C$_1$-C$_{20}$ heterocycloalkyl, C$_1$-C$_{20}$ heterocycloalkenyl, aryl and heteroaryl.

4. The method as claimed in claim 1, wherein the aldehyde is represented by a structure formula (2):

wherein R$_2$ is a member selected from the group consisting of C$_1$-C$_{10}$ alkyl, C$_2$-C$_{10}$ alkenyl, C$_2$-C$_{10}$ alkynyl, C$_3$-C$_{20}$ cycloalkyl, C$_3$-C$_{20}$ cycloalkenyl, C$_1$-C$_{20}$ heterocycloalkyl, C$_1$-C$_{20}$ heterocycloalkenyl, aryl and heteroaryl.

5. The method as claimed in claim 1, wherein the bidentate ligand contains phosphor.

6. The method as claimed in claim 5, wherein the bidentate ligand comprises DPPE, (R)-Prophos, (R)-Tol-BINAP, (S)-BINAP, (S,S)-Chiraphos, (R,R)-Ph-BPE, (R)-Quinap, (R)-MOP, (S,S)-DIPAMP, (R)-Monophos, (R,R)-BDPP or (S,S)-DIOP.

7. The method as claimed in claim 1, wherein the cobalt ion is Co$^{2+}$.

8. The method as claimed in claim 1, wherein the cobalt ion is provided by Co(acac)$_2$, CoI$_2$, CoBr$_2$ or CoCl$_2$.

9. The method as claimed in claim 1, wherein the reaction reagent is basic.

10. The method as claimed in claim 9, wherein the basic reaction reagent is provided by K$_2$CO$_3$.

11. An enantioselective method for synthesis of secondary alcohols, comprising:
    reacting an organoboronic acid and an aldehyde in an organic reagent to obtain an enantioselective secondary alcohol, wherein the organic reagent comprises a cobalt ion and a chiral bidentate ligand.

12. The method as claimed in claim 11, wherein the organoboronic acid is an arylboronic acid.

13. The method as claimed in claim 11, wherein the organoboronic acid is a phenylboronic acid represented by a structure formula (1):

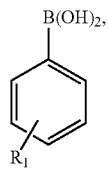

(1)

wherein $R_1$ is a member selected from the group consisting of H, halo, cyano, trifluoromethyl, amino, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl and heteroaryl.

14. The method as claimed in claim 11, wherein the aldehyde is represented by a structure formula (2):

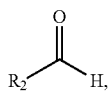

(2)

wherein $R_2$ is a member selected from the group consisting of $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl and heteroaryl.

15. The method as claimed in claim 11, wherein the bidentate ligand contains phosphor.

16. The method as claimed in claim 15, wherein the bidentate ligand comprises (R)-Prophos, (R)-Tol-BINAP, (S)-BINAP, (S,S)-Chiraphos, (R,R)-Ph-BPE, (R)-Quinap, (R)-MOP, (S,S)-DIPAMP, (R)-Monophos, (R,R)-BDPP or (S,S)-DIOP.

17. The method as claimed in claim 11, wherein the cobalt ion is $Co^{2+}$.

18. The method as claimed in claim 11, wherein the cobalt ion is provided by $Co(acac)_2$, $CoI_2$, $CoBr_2$ or $CoCl_2$.

19. The method as claimed in claim 11, wherein the organic reagent is basic.

20. The method as claimed in claim 19, wherein the basic organic reagent is provided by $K_2CO_3$.

* * * * *